United States Patent
Ryan et al.

(10) Patent No.: US 12,070,561 B2
(45) Date of Patent: *Aug. 27, 2024

(54) APPARATUS FOR USE IN A MEDICAL PROCEDURE IN THE VASCULATURE COMPRISING A GUIDEWIRE AND A CATHETER AND A METHOD OF USING THE SAME

(71) Applicant: C.R. Bard, Inc., Tempe, AZ (US)

(72) Inventors: Eoin Ryan, Dublin (IE); Allan Ronan, Wexford (IE)

(73) Assignee: C.R. Bard, Inc., Franklin Lakes, NJ (US)

( * ) Notice: Subject to any disclaimer, the term of this patent is extended or adjusted under 35 U.S.C. 154(b) by 484 days.

This patent is subject to a terminal disclaimer.

(21) Appl. No.: 17/208,577

(22) Filed: Mar. 22, 2021

(65) Prior Publication Data

US 2021/0220610 A1 Jul. 22, 2021

Related U.S. Application Data

(63) Continuation of application No. 15/779,199, filed as application No. PCT/EP2015/078036 on Nov. 30, 2015, now Pat. No. 11,052,225.

(51) Int. Cl.
*A61M 25/01* (2006.01)
*A61M 25/09* (2006.01)
*A61M 25/10* (2013.01)

(52) U.S. Cl.
CPC .... *A61M 25/0127* (2013.01); *A61M 25/0108* (2013.01); *A61M 25/09* (2013.01); *A61M 25/09041* (2013.01); *A61M 25/10* (2013.01); *A61M 2025/09125* (2013.01); *A61M 2025/09175* (2013.01); *A61M 2025/105* (2013.01); *A61M 2205/0288* (2013.01)

(58) Field of Classification Search
CPC .............. A61M 25/01; A61M 25/0127; A61M 25/09041; A61M 2025/0166; A61M 2025/0288; A61M 2025/09125
See application file for complete search history.

(56) References Cited

U.S. PATENT DOCUMENTS

| | | | |
|---|---|---|---|
| 5,623,943 A * | 4/1997 | Hackett | A61M 25/0169 600/585 |
| 11,052,225 B2 * | 7/2021 | Ryan | A61M 25/0108 |
| 2015/0011834 A1 * | 1/2015 | Ayala | A61B 17/0218 29/428 |
| 2015/0190615 A1 * | 7/2015 | Shaltis | A61M 25/09 604/95.04 |
| 2015/0202408 A1 * | 7/2015 | McMurtry | A61M 25/01 604/95.01 |

\* cited by examiner

*Primary Examiner* — Chelsea E Stinson
*Assistant Examiner* — Anh Bui
(74) *Attorney, Agent, or Firm* — Dickinson Wright PLLC; Andrew D. Dorisio

(57) ABSTRACT

There is provided an apparatus for use in a bodily lumen. The apparatus comprises a guidewire and a catheter. The guidewire has a proximal end portion and a distal end portion. The catheter has a proximal end portion and a distal end portion. The catheter includes a lumen for receiving the guidewire. The catheter is configured to be translated along the guidewire. The catheter is configured to be biased towards a translated position along the guidewire by a magnetic attraction between the guidewire and the catheter.

20 Claims, 4 Drawing Sheets

APPARATUS FOR USE IN A MEDICAL PROCEDURE IN THE VASCULATURE COMPRISING A GUIDEWIRE AND A CATHETER AND A METHOD OF USING THE SAME

This application is a continuation of U.S. application Ser. No. 15/779,199, filed on May 25, 2018, which is a National Stage of PCT/EP2015/078036, filed on Nov. 30, 2015.

TECHNICAL FIELD

The present disclosure generally relates to an apparatus for use in a medical procedure in the vasculature, and particularly to an apparatus comprising a guidewire and a catheter, where the catheter is biased towards a translated position along the guidewire by a magnetic attraction between the guidewire and the catheter. The present disclosure also generally relates to a method of performing a medical procedure in the vasculature.

BACKGROUND OF THE DISCLOSURE

Typically, a guidewire and a catheter may be used in a medical procedure in the vasculature so as to treat a treatment site of the vasculature. For example, a guidewire may be placed in the vasculature and a catheter may be translated along the guidewire such that the catheter is placed relative to the treatment site. The catheter and any associated medical devices may be used for the treatment of the treatment site in the medical procedure. In such medical procedures, the accuracy of the final placement of the catheter relative to the treatment site may be important to the success of the medical procedure. Accordingly, any geographic misalignment of the catheter in the vasculature, i.e., any error in the final position of the catheter relative to the treatment site, may severely reduce the success rate of the medical procedure.

Accordingly, there is a need for an apparatus in which a catheter may be placed into the vasculature relative to a treatment site with enhanced accuracy. There is also a need for a method in which a catheter may be placed into the vasculature relative to a treatment site with enhanced accuracy.

BRIEF DESCRIPTION OF THE DRAWINGS

For a better understanding of the present disclosure, and to show how the same may be carried into effect, reference will be made, by way of example only, to the following drawings, in which.

DETAILED DESCRIPTION

Figure 1A:
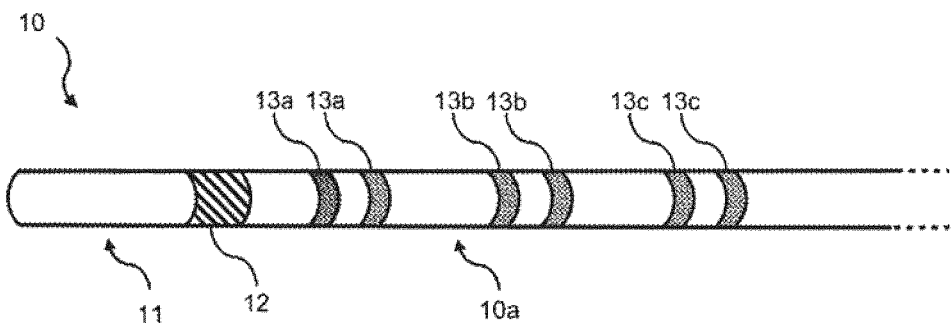
FIG. 1a shows a guidewire according to an embodiment of the present disclosure.

In one embodiment, there is provided an apparatus for use in a bodily lumen. The apparatus comprises a guidewire and a catheter. The guidewire has a proximal end portion and a distal end portion. The catheter has a proximal end portion and a distal end portion. The catheter includes a lumen for receiving the guidewire. The catheter is configured to be translated along the guidewire. The catheter is configured to be biased towards a translated position along the guidewire by a magnetic attraction between the guidewire and the catheter.

Throughout this disclosure, the term 'magnetic attraction between the guidewire and the catheter' refers to a force between the guidewire and the catheter caused by a magnetic field and which acts to force the guidewire and the catheter together.

In one embodiment, the guidewire and/or the catheter includes a magnet.

Throughout this disclosure, the term 'magnet' refers to any element capable of producing a magnetic field. For example, a permanent magnet or an electromagnet.

In one embodiment, the guidewire and/or the catheter includes a magnetically responsive element.

In one embodiment, the guidewire includes a magnet and the catheter includes a magnetically responsive element. In one embodiment, the guidewire includes a magnetically responsive element and the catheter includes a magnet. In one embodiment, the guidewire includes a magnet and the catheter includes another magnet.

Throughout this disclosure, the term 'magnetically responsive element' may refer to any element which may experience a force when in a magnetic field. In particular, a 'magnetically responsive element' does not create its own magnetic field.

In one embodiment, the magnetically responsive element is a ferromagnet.

In one embodiment, the catheter is biased towards only the translated position.

In one embodiment, the magnetic attraction between the guidewire and the catheter is the greatest at the translated position.

In one embodiment, the magnetic attraction between the guidewire and the catheter is due to a magnetic attraction between the distal end portion of the guidewire and the distal end portion of the catheter.

In one embodiment, the guidewire comprises a radiopaque marker.

In one embodiment, the distance between the translated position and the radiopaque marker is a fixed predetermined distance.

In one embodiment, apparatus comprises a balloon supported by the distal end portion of the catheter.

In one embodiment, the magnetic attraction between the guidewire and the catheter is due to a magnetic attraction between the guidewire and a portion of the catheter which is distal to the balloon.

In one embodiment, the catheter includes a magnet or a magnetically responsive element. The magnet or the magnetically responsive element is disposed within the lumen of the catheter. In one embodiment, the catheter includes a magnet or a magnetically responsive element, and wherein, a surface of the magnet or a surface of the magnetically responsive element forms part of the lumen.

In one embodiment, the guidewire includes a magnet or a magnetically responsive element, and wherein, a surface of the magnet or a surface of the magnetically responsive element forms part of the outer surface of the guidewire.

In one embodiment, the catheter may be biased towards the translated position along the guidewire when the guidewire is received in the lumen.

In one embodiment, the translated position is a position along the length of the guidewire.

In one embodiment, the catheter is biased along a direction along the length of the guidewire.

In one embodiment, the magnetically responsive element is a magnetically responsive material as a ferromagnetic material.

In one embodiment, any of the magnet (s) and/or the magnetically responsive element (s) may be ring magnet (s) or ring-shaped elements, respectively.

In one embodiment, the magnet (s) and/or the magnetically responsive element (s) may be disposed in the distal end portion of the catheter and/or the distal end portion of the guidewire.

In one embodiment, another translated position in which the catheter is biased, different to the translated position, does not exist.

In one embodiment, the catheter is biased towards N translated positions along the guidewire, where N is any positive integer smaller than infinity.

In one embodiment, the magnetic attraction between the guidewire and the catheter is smaller at any translated position other than the translated position.

In one embodiment, the guidewire comprises at least two radiopaque markers.

Throughout this disclosure, a distance/length along the guidewire between two points may be defined when the guidewire is in a straight or curved configuration. Specifically, a distance/length along the guidewire between two points may be defined as the distance/length of the guidewire between the two points on the guidewire. For example, if the guidewire is in a curved configuration, the distance/length along the guidewire between two points may be the distance/length along the curve formed by the guidewire between the two points.

Throughout this disclosure, a distance/length along the catheter between two points may be defined when the catheter is in a straight or curved configuration. Specifically, a distance/length along the catheter between two points may be defined as the distance/length of the catheter between the two points on the catheter. For example, if the catheter is in a curved configuration, the distance/length along the catheter between two points would be the distance/length along the curve formed by the catheter between the two points.

It will be clear to a skilled person that the configurations relating to the magnets contained throughout this disclosure may be applicable to a magnet, a magnetically responsive element and/or a magnetically responsive material.

Any of the above embodiments may be combined with any other of the embodiments, where appropriate to the skilled person.

In another embodiment, there is provided a method for performing a procedure in a bodily lumen. The method comprises positioning a guidewire in the vasculature. The method comprises translating a catheter along the guidewire. The method comprises basing the catheter towards a translated position along the guidewire by a magnetic attraction between the guidewire and the catheter.

In one implementation, the guidewire comprises a radiopaque marker. In one implementation, the step of positioning comprises positioning the radiopaque marker relative to a desired treatment site.

In one implementation, the guidewire comprises a magnet and/or a magnetically responsive element. In one implementation, the catheter comprises a magnet and/or a magnetically responsive element. In one implementation, the step of positioning comprises positioning the magnet and/or the magnetically responsive element of the guidewire relative to a desired treatment site.

In one implementation, the magnetically responsive element is a ferromagnet.

In one implementation, the guidewire is the guidewire of any of the previous embodiments.

In one implementation, the catheter is the catheter of any of the previous embodiments.

Any of the above implementations may be combined with any other of the implementations, where appropriate to the skilled person.

Throughout this disclosure 'a bodily lumen' may be a lumen in the vasculature.

Throughout this disclosure 'a translated position' may be 'a first translated position'.

Further features of the embodiments of the apparatus according to the present disclosure will be evident from the following description of certain embodiments. In the description of these embodiments, reference is made to the accompanying drawings. Like parts of the various embodiments are numbered with like references.

FIG. 1a shows a portion of a guidewire 10 according to an embodiment of the present disclosure. FIG. 1a shows a distal end portion 10a of the guidewire 10.

The guidewire 10 has a guidewire body 11. The guidewire body 11 is in the form of a wire. The guidewire 10, and specifically the guidewire body 11, is sufficiently flexible such that it may bend during translation along any curves in the vasculature. Also, the guidewire 10, and specifically the guidewire body 11, is stiff enough such that the distal end portion 10a may be translated in the vasculature by a movement of a proximal end portion (not shown) of the guidewire 10.

The distal end portion 10a of the guidewire 10 has a guidewire magnet 12. In this embodiment, the guidewire magnet 12 is a ring magnet. The guidewire magnet 12 creates a magnetic field in the vicinity around the guidewire magnet 12.

The distal end portion 10a of the guidewire 10 has first radiopaque markers 13a, second radiopaque markers 13b and third radiopaque markers 13c spaced apart along the length of the guidewire 10. In this embodiment, the distances along the length of the guidewire 10 between the first radiopaque markers 13a and the second radiopaque markers 13b; and the second radiopaque markers 13b and the third radiopaque markers 13c, are equal. In this embodiment, the first radiopaque markers 13a, the second radiopaque markers 13b and the third radiopaque markers 13c each have two radiopaque markers. In this embodiment, each of the radiopaque markers take the form of a ring. In alternative embodiments, the first radiopaque markers 13a, the second radiopaque markers 13b and the third radiopaque markers 13c may consist of one radiopaque marker each.

The distances along the length of the guidewire 10 between the guidewire magnet 12 and each of the radiopaque markers is fixed. These distances may be known/determined by a practitioner.

The guidewire 10 is configured such that the practitioner may steer the guidewire 10 through a patient's vasculature until the distal end portion 10a of the guidewire 10 is positioned at a desired location in the patient's vasculature, for example, in the vicinity of a treatment site.

Figure 1B:
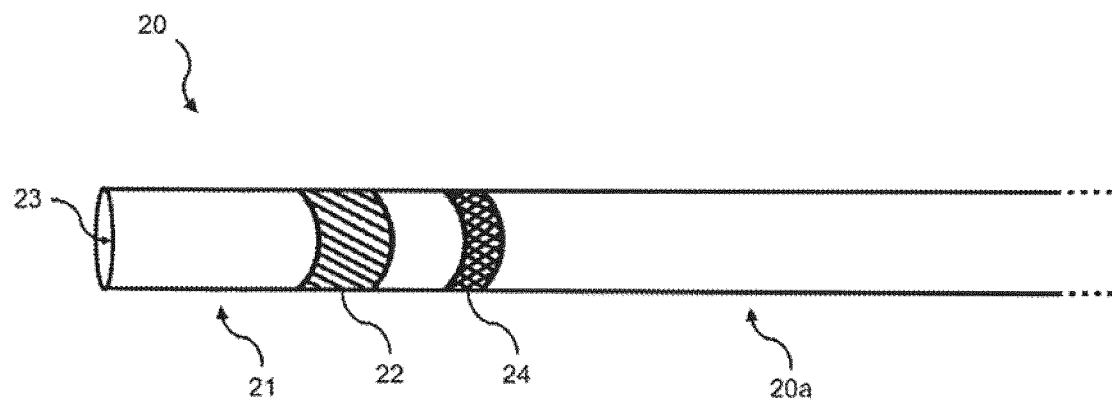
FIG. 1b shows a catheter according to an embodiment of the present disclosure.

As will be clear to a person skilled in the art, the first radiopaque markers 13a, the second radiopaque markers 13b and/or the third radiopaque markers 13c may be used so as to verify the location of the distal end portion 10a, and, specifically, the guidewire magnet 12, relative to the patient's vasculature, FIG. 1b shows a portion of the catheter 20 according to an embodiment of the present disclosure. FIG. 1b shows a distal end portion 20a of the catheter 20.

The catheter 20 has a catheter shaft 21. The catheter 20, and specifically the catheter shaft 21, is sufficiently flexible such that it may bend during translation along any curves in the vasculature. Also, the catheter 20, and specifically the catheter shaft 21, is stiff enough such that the distal end portion 20a may be translated in the vasculature by a movement of a proximal end portion (not shown) of the catheter 20.

The catheter 20 has a lumen 23 which extends along the length of the catheter 20. The lumen 23 is configured to receive the guidewire 10 shown in FIG. 1a. The catheter 20 is configured to be translated along the guidewire 10. For example, during a medical procedure, once the guidewire 10 has been placed in the vasculature, the proximal end portion (not shown) of the guidewire 10 may be inserted into a distal end portion of the lumen 23 of the catheter 20. The catheter 20 may then be translated along the guidewire 10 by a corresponding translation of the proximal end portion (not shown) of the catheter 20.

The catheter 20 has a treatment device 24 which may be used to treat a treatment site when the catheter 20 is placed in the vasculature. Various treatment devices 24 will be known to a person skilled in the art.

The catheter 20 has a catheter magnet 22 disposed in the distal end portion 20a of the catheter 20. In this embodiment, the catheter magnet 22 is a ring magnet. The catheter magnet 22 creates a magnetic field in the vicinity around the catheter magnet 22, and, in particular, in the lumen 23 of the catheter 20. The distance along the length of the catheter 20 between the catheter magnet 22 and the treatment device 24 is fixed. This distance may be known/determined by a practitioner.

The guidewire magnet 12 and the catheter magnet 22 are configured to be magnetically attracted to each other. Accordingly, there is a magnetic attraction between the guidewire 10 and the catheter 20, and, in particular, the distal end portion 10a of the guidewire 10 and the distal end portion 20a of the catheter 20. Therefore, as the guidewire 10 is received in the lumen 23 and the catheter 20 is translated along the guidewire 10, the catheter 20 may be biased towards a translated position along the guidewire 10. Hence, with such a configuration, the catheter 20 is biased towards a translated position along the guidewire 10 by a magnetic attraction between the guidewire 10 and the catheter 20.

As the catheter 20 is biased towards the translated position along the guidewire 10, it may be possible to configure the present embodiment such that the catheter 20 and the guidewire 10 snap fit into alignment with one another (at the translated position) as the guidewire magnet 12 and the catheter magnet 22 come into close proximity to one another. In the aligned configuration, the guidewire magnet 12 and the catheter magnet 22 may align/overlap with one another. In the aligned configuration, the guidewire magnet 12 and the catheter magnet 22 are in their equilibrium relative position. Hence, the guidewire 10 and the catheter 20 are also in their equilibrium relative position (the translated position).

In this embodiment, the catheter 20 is biased towards only the translated position. In other words, the catheter 20 is not biased towards any translated position other than the translated position. In this embodiment, the magnetic attraction between the guidewire magnet 12 and the catheter magnet 22 is the greatest at the translated position.

Figure 2A:
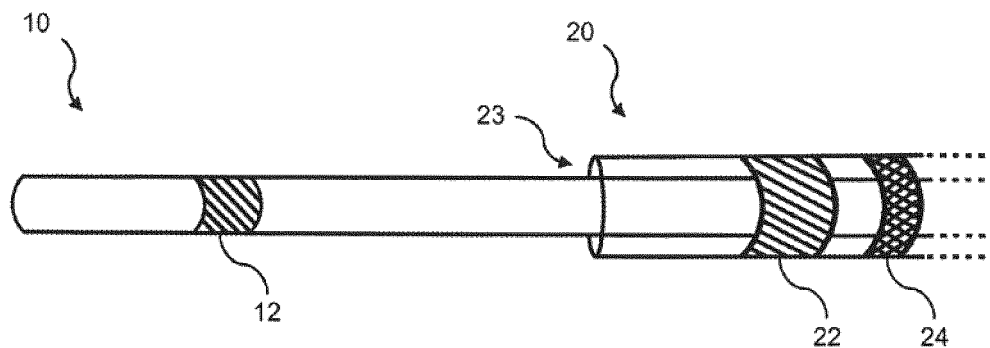
FIGS. 2a to 2c show the catheter being translated along the guidewire.
Figure 2B:
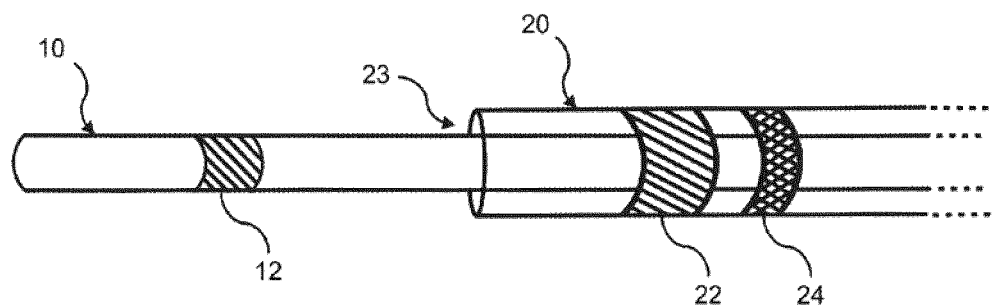
Figure 2C:
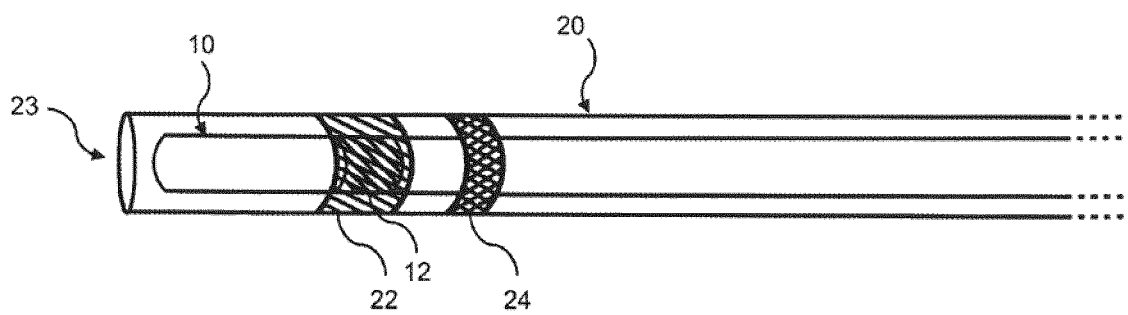

FIGS. 2a to 2c show the catheter 20 being translated along the guidewire 10. In FIGS. 2a to 2c, the radiopaque markers are not shown.

FIG. 2a shows a state in which the proximal end portion (not shown) of the guidewire 10 has been inserted into the distal end portion of the lumen 23 of the catheter 20, and the catheter 20 has been translated a distance along the guidewire 10.

FIG. 2b shows a state in which the catheter 20 has been further translated along the guidewire 10. This may be achieved by the practitioner translating a proximal portion of the catheter 20 such that the distal end portion of the catheter is translated along the guidewire 10.

FIG. 2c shows a state in which the guidewire magnet 12 and the catheter magnet 22 are in their equilibrium relative position. In this state, the guidewire 10 and the catheter 20 are also in their equilibrium relative position (the translated position). In other words, in the state shown in FIG. 2c, the catheter 20 is in the translated position along the guidewire 10. In states where the catheter 20 is in a translated position close to the translated position (such as that shown in FIG. 2b), the catheter 20 may experience strong biasing towards the translated position due to the magnetic attraction between the guidewire magnet 12 and the catheter magnet 22. In such states, the catheter 20 is biased so as to snap fit such that it is in the state shown in FIG. 2c.

Figure 3:
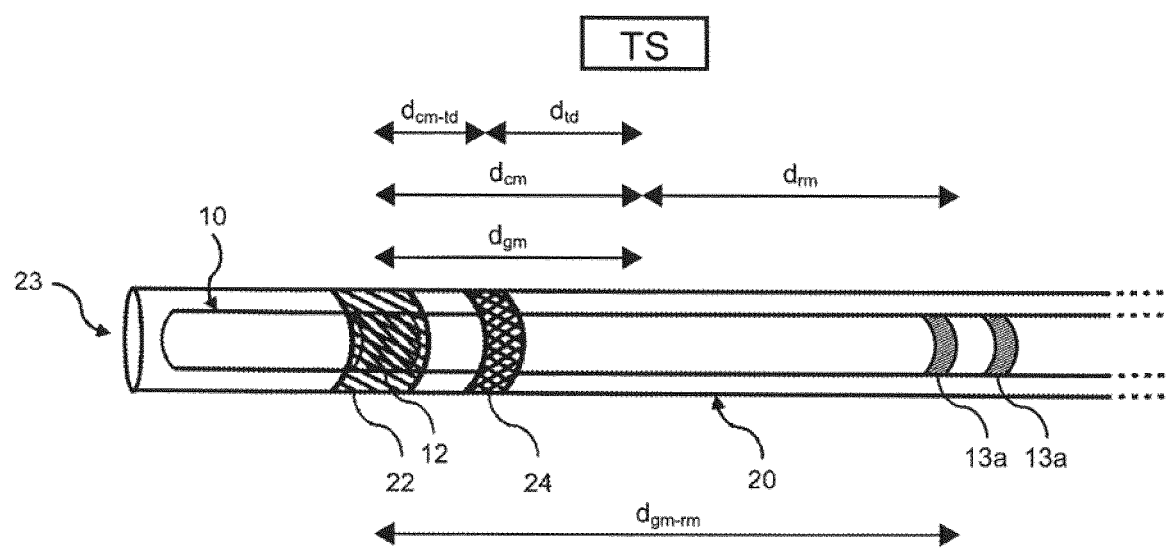
FIG. 3 shows a state of the guidewire and the catheter in which the guidewire magnet and the catheter magnet are in an equilibrium relative position.

FIG. 3 also shows the state in which the guidewire magnet 12 and the catheter magnet 22 are in their equilibrium relative position. In this state, the guidewire 10 and the catheter 20 are also in their equilibrium relative position (the translated position). FIG. 3 further shows a treatment site TS. FIG. 3 also shows certain distances which may aid in the correct placement of the treatment device 24 relative to the treatment site TS during a medical procedure.

The distance $d_{rm}$ shows the distance between the radiopaque markers 13a and the treatment site TS. The distance $d_{gm}$ shows the distance between the guidewire magnet 12 and the treatment site TS. The distance $d_{cm}$ shows the distance between the catheter magnet 22 and the treatment site TS. The distance $d_{td}$ shows the distance between the treatment device 24 and the treatment site TS. The distance dem-td shows the distance along the catheter 20 between the catheter magnet 22 and the treatment device 24. The distance $d_{gm\text{-}rm}$ shows the distance along the guidewire 10 between the guidewire magnet 12 and the radiopaque markers 13a.

The practitioner may wish to place the treatment device 24 at a correct distance $d_{td}$ from the treatment site TS ($d_{td}$ may equal zero). As the distance $d_{cm\text{-}td}$ is known, the correct final distance $d_{cm}$ may be calculated (using $d_{cm}=d_{cm\text{-}td}+d_{td}$). Accordingly, the correct final distance $d_{gm}$ may also be calculated—this will be the same as correct final distance $d_{cm}$ (i.e., $d_{gm}=d_{cm}$). As the distance $d_{gm\text{-}rm}$ is known, the correct final distance $d_{rm}$ may be calculated (using $d_{rm}=d_{gm\text{-}rm}-d_{gm}$). Therefore, a practitioner wishing to place the treatment device 24 at a correct distance $d_{td}$ from the treatment site TS, may calculate the correct final distance $d_{rm}$ such that the guidewire 10 may be correctly placed in the vasculature. Once the guidewire 10 is placed in the vasculature, the catheter 20 may be translated along the guidewire 10. As the catheter 20 is biased towards the translated position along the guidewire 10, during translation, the catheter 20 may snap fit into the state shown in FIG. 2c. Accordingly, the treatment device 24 will be correctly placed relative to the treatment site TS.

Figure 4:
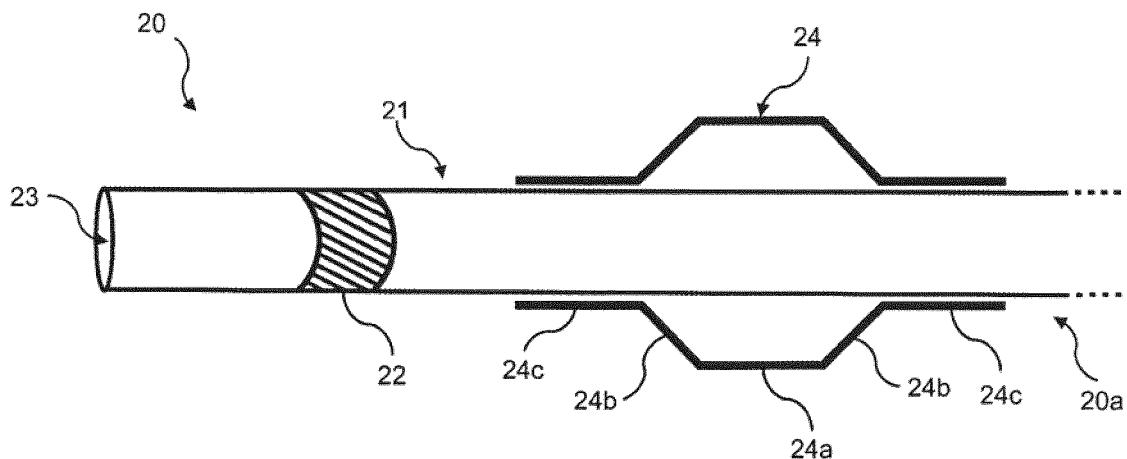
FIG. 4 shows a catheter according to another embodiment of the present disclosure.

FIG. 4 shows a catheter 20 according to another embodiment of the present disclosure. The catheter 20 shown in FIG. 4 is similar to the previous embodiment, and, accordingly, only certain differences will be explained below. The catheter 20 shown in FIG. 4 may be configured to receive the guidewire 10 described with respect to FIG. 1a.

In the catheter 20 shown in FIG. 4, the treatment device 24 is a balloon. Balloon 24 is mounted on the catheter shaft 21 of the catheter 20. The balloon 24 has an intermediate section 24a, or "barrel" having a working surface, and end sections 24b. The working surface is the surface of the balloon 24 that is used to achieve a desired treatment effect. In this embodiment, the end sections 24b may reduce in diameter to join the intermediate section 24a to the catheter shaft 21 such that the balloon 24 is in a deflated state. In an inflated state, such as that shown in FIG. 4, the end sections 24b have an increased diameter such that the intermediate section 24a is separated from the catheter shaft 21. The balloon 24 is sealed to the catheter shaft 21 at balloon ends 24c to allow the inflation of the balloon 24 via one or more inflation lumens (not shown) which extend within the catheter shaft 21 and which communicate with the interior of the balloon 24.

In this embodiment, the catheter magnet 22 is disposed distally of the balloon 24. Optionally, the catheter magnet 22 is disposed in close proximity to the balloon 24. The distance along the length of the catheter 20 between the catheter magnet 22 and the balloon 24 is fixed. This distance may be known/determined by a practitioner.

The apparatus comprising the catheter 10 shown in FIG. 4 and the guidewire 10 shown in FIG. 1a may be particularly useful in medical procedures for treating a lesion. Typically, a catheter including a drug-coated balloon is aligned with the lesion and then inflated so as to come into contact with the lesion. The drug may be transferred to the lesion so as to treat the lesion in some manner. However, any geographic misalignment (i.e. any error in the final position of the balloon relative to the lesion), may severely reduce the success rate of the medical procedure as the drug may not be as effective. In cases where geographic misalignment occurs, restenosis is seen at significantly greater levels than with lesions where geographic misalignment did not occur. Furthermore, in such treatments of a lesion, the drug-coated balloon is typically oversized relative to the lesion so as to ensure the drug contacts the whole length of the lesion. However, this may result in the treatment of a non-treatment site which extends beyond the lesion.

The apparatus comprising the catheter 10 shown in FIG. 4 and the guidewire 10 shown in FIG. 1a may solve all or some of the above problems associated with typical treatments of lesions using drug-coated balloons.

For example, as the distances along the guidewire 10 between the first radiopaque markers 13a, second radiopaque markers 13b and third radiopaque markers 13c are known, the radiopaque markers may be used as an internal ruler to measure the length of the lesion. Specifically, the guidewire 10 may be steered through the vasculature until some/all of the radiopaque markers are positioned adjacent to the lesion. Then, using X-ray apparatus whilst the guidewire 10 is positioned, an image of the lesion with the radiopaque markers may be used to measure the length of the lesion. Accordingly, the size of the balloon 24 may be selected depending on the measured length of the lesion.

Further, as the distance along the guidewire 10 between the guidewire magnet 12 and the radiopaque markers is known, as explained above in relation to FIG. 3, the correct final position of the guidewire magnet 12 can be predicted from measurements of the locations of the radiopaque markers. Further, as the distance along the catheter 20 between the catheter magnet 22 and the balloon 24 is also known, once the guidewire magnet 12 and the catheter magnet 22 are in their equilibrium relative position, the location of the balloon 24 may be accurately predicted. Hence, the practitioner may calculate the ideal locations of the radiopaque markers relative to the lesion so as to improve the effect of the drug.

Although the above explanation is considered to fully clarify how the present disclosure may straight-forwardly be put into effect by those skilled in the art, it is to be regarded as purely exemplary. In particular, there are a number of variations which are possible, as may be appreciated by those skilled in the art.

For example, even though the above embodiments have been described with a guidewire 10 comprising a guidewire magnet 12 and the catheter comprising a catheter magnet 22, it will be evident to the skilled person that the catheter 20 merely has to be biased towards a translated positon along the guidewire 10 by a magnetic attraction between the guidewire 10 and the catheter 20. This magnetic attraction may result by any means. Accordingly, the catheter 20 may include a magnet and the guidewire 10 may include a magnetically responsive element; or the catheter 20 may include magnetically responsive element and the guidewire 10 may include a magnet.

Further, the guidewire magnet 12 and/or the catheter magnet 22 may not be ring magnets. Alternatively, the guidewire magnet 12 and/or the catheter magnet 22 may be bar magnets. Also, the guidewire magnet 12 and/or the catheter magnet 22 need not be permanent magnets; instead, either or both magnets 12, 22 may be electromagnets.

The guidewire magnet 12 may be disposed in the guidewire body 11 in a variety of configurations. For example, the guidewire magnet 12 may be attached to an outer surface of the guidewire body 11. The guidewire magnet 12 may form integral part of the guidewire body 11.

The catheter magnet 22 may be disposed in the catheter shaft 21 in a variety of configurations. For example, the catheter magnet 22 may be attached to an inner surface of the lumen 23. The catheter magnet 22 may form an integral part of the catheter shaft 21.

In an embodiment in which the guidewire magnet 12 and/or the catheter magnet 22 are electromagnets, the catheter is configured to be biased towards the translated positon. In such a configuration, the catheter is biased towards the translated positon when the electromagnet (s) are switched on.

In another embodiment, the guidewire 10 has two or more magnets and the catheter 20 has a corresponding number of magnets. In such a configuration, the catheter may be biased towards two or more translated positions. Again, any of the magnets may be replaced with magnetically responsive elements.

In another embodiment, the guidewire magnet 12 and the catheter magnet 22 are configured such that there is a gap between the guidewire 10 and the lumen 23 between the magnets 12, 22 when the magnets 12, 22 are in their equilibrium relative position.

The guidewire 10 may comprise a single radiopaque marker, rather than the three pairs of radiopaque markers 13a, 13b, 13c shown in FIG. 1a.

The lumen 23 may not be a central lumen, as in the above embodiments; rather, lumen 23 may be offset from the central axis of the catheter shaft 21. Further, the lumen 23 may not extend along the whole length of the catheter 20; rather, the lumen 23 may extend along a portion of the length of the catheter 20, in particular, along the distal end portion 20a of the catheter 20.

All of the above are fully within the scope of the present disclosure, and are considered to form the basis for alternative embodiments in which one or more combinations of the above described features are applied, without limitation to the specific combinations disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptions fall within the scope of the present disclosure.

The invention claimed is:

1. An apparatus for use in a bodily lumen, comprising:
a guidewire having a proximal end portion and a distal end portion; and
a catheter having a proximal end portion and a distal end portion, the catheter including a lumen for receiving the guidewire,
wherein the catheter is configured to translate along the guidewire from a first location to a second, translated location as a result of a magnetic attraction between the guidewire and the catheter, and wherein the catheter and the guidewire are configured to snap fit into alignment with each other at the second, translated location.

2. The apparatus of claim 1, wherein the guidewire and/or the catheter includes a magnet.

3. The apparatus of claim 1, wherein the guidewire and/or the catheter includes a magnetically responsive element.

4. The apparatus of claim 3, wherein the magnetically responsive element is a ferromagnet.

5. The apparatus of claim 1, wherein the catheter is biased towards only the translated position.

6. The apparatus of claim 1, wherein the magnetic attraction between the guidewire and the catheter is the greatest at the translated position.

7. The apparatus of claim 1, wherein the magnetic attraction between the guidewire and the catheter is due to a magnetic attraction between the distal end portion of the guidewire and the distal end portion of the catheter.

8. The apparatus of claim 1, wherein the guidewire comprises a radiopaque marker.

9. The apparatus of claim 8, wherein the distance between the second translated location and the radiopaque marker is a fixed predetermined distance.

10. The apparatus of claim 1, comprising a balloon supported by the distal end portion of the catheter.

11. The apparatus of claim 10, wherein the magnetic attraction between the guidewire and the catheter is due to a magnetic attraction between the guidewire and a portion of the catheter which is distal to the balloon.

12. The apparatus of claim 1, wherein the catheter includes a magnet or a magnetically responsive element, and wherein the magnet or the magnetically responsive element is disposed within the same lumen of the catheter for receiving the guidewire and not another adjacent lumen.

13. The apparatus of claim 1, wherein the catheter includes a magnet or a magnetically responsive element, wherein a surface of the magnet or a surface of the magnetically responsive element forms part of the lumen of the catheter.

14. The apparatus of claim 1, wherein the guidewire includes a magnet or a magnetically responsive element, and wherein a surface of the magnet or a surface of the magnetically responsive element forms part of the outer surface of the guidewire.

15. The apparatus of claim 1, wherein the catheter and/or the guidewire includes a magnet or a magnetically responsive element, and wherein the magnet or the magnetically responsive element is a ring magnet or a ring-shaped element, respectively.

16. A method for performing a procedure in a bodily lumen, comprising:
positioning a guidewire having a proximal end portion and a distal end portion in the vasculature;
translating a catheter along the guidewire, the catheter having a proximal end portion and a distal end portion, the catheter including a lumen for receiving the guidewire,
the translating being from a first location to a second, translated location as a result of a magnetic attraction between the guidewire and the catheter such that the catheter and the guidewire snap fit into alignment with each other at the second, translated location.

17. The method of claim 16, wherein the guidewire comprises a radiopaque marker, and wherein the step of positioning comprises positioning the radiopaque marker relative to a desired treatment site.

18. The method of claim 16, wherein the guidewire comprises a magnet and/or a magnetically responsive element, wherein the catheter comprises a magnet and/or a magnetically responsive element, and wherein the step of positioning comprises positioning the magnet and/or the magnetically responsive element of the guidewire relative to a desired treatment site.

19. The method of claim 16, wherein the magnetically responsive element is a ferromagnet.

20. An apparatus for use in a bodily lumen, comprising:
a guidewire having a proximal end portion and a distal end portion; and
a catheter having a proximal end portion and a distal end portion, the catheter including a lumen for receiving the guidewire, the catheter being configured to be translated along the guidewire,
wherein the catheter is configured to translate along the guidewire from a first location to a second, translated location as a result of a magnetic attraction between the guidewire and the catheter created by a magnet disposed within the lumen for receiving the guidewire and not an adjacent lumen, and wherein the catheter and the guidewire are configured to snap fit into alignment with each other.

* * * * *